United States Patent [19]
Olovson et al.

[11] Patent Number: 5,423,757
[45] Date of Patent: Jun. 13, 1995

[54] SYRINGE, HAVING A ROD AND A PISTON AND A DISCONNECT MECHANISM

[76] Inventors: Gudmar Olovson, 64 Rue Saint Charles, 75015 Paris, France; Nils G. Helldin, Västergatan 46, 533 22 Götene, Sweden

[21] Appl. No.: 137,002
[22] PCT Filed: Apr. 21, 1992
[86] PCT No.: PCT/SE92/00258
§ 371 Date: Oct. 13, 1993
§ 102(e) Date: Oct. 13, 1993
[87] PCT Pub. No.: WO92/18180
PCT Pub. Date: Oct. 29, 1992

[30] Foreign Application Priority Data

Apr. 22, 1991 [SE] Sweden .................. 9101204
Apr. 22, 1991 [SE] Sweden .................. 9101205

[51] Int. Cl.⁶ .................. A61M 5/50; A61M 5/00
[52] U.S. Cl. .................. 604/110; 604/218; 604/228
[58] Field of Search ........... 604/110, 218, 228, 195, 604/196

[56] References Cited
U.S. PATENT DOCUMENTS

| 4,906,231 | 3/1990 | Young . |
| 4,908,020 | 3/1990 | Pettersen .................. 604/110 |
| 4,911,695 | 3/1990 | Lindner .................. 604/228 |
| 5,004,460 | 4/1991 | Gimeno . |
| 5,007,904 | 4/1991 | Densmore et al. .................. 604/228 |
| 5,032,114 | 7/1991 | Olovson . |
| 5,059,179 | 10/1991 | Quatrochi et al. .................. 604/110 |
| 5,085,638 | 2/1992 | Farbstein et al. .................. 604/110 |
| 5,094,148 | 3/1992 | Haber et al. .................. 92/29 |
| 5,171,300 | 12/1992 | Blake, III et al. .................. 604/110 |

FOREIGN PATENT DOCUMENTS

| 0229017 | 7/1987 | European Pat. Off. . |
| 2381527 | 9/1978 | France . |
| 163263 | 1/1990 | Norway . |
| 438598 | 3/1979 | Sweden . |
| WO89/04677 | 6/1989 | WIPO . |

*Primary Examiner*—John D. Yasko
*Assistant Examiner*—Adam J. Cermak
*Attorney, Agent, or Firm*—Burns, Doane, Swecker & Mathis

[57] ABSTRACT

The invention relates to a disposable syringe which comprises a rod (5) that can be moved reciprocatingly in relation to a container (2). One end of the rod has the form of a needle (3), or can coact with a needle (3). The syringe also includes a piston (4) which coacts with the rod and which has means (6) for connecting the piston to the rod and disconnecting the piston therefrom. The rod (5) has an angled cross section and is provided with support and/or slide surfaces which coact with support and/or slide surfaces positioned peripherally on the piston (4).

10 Claims, 3 Drawing Sheets

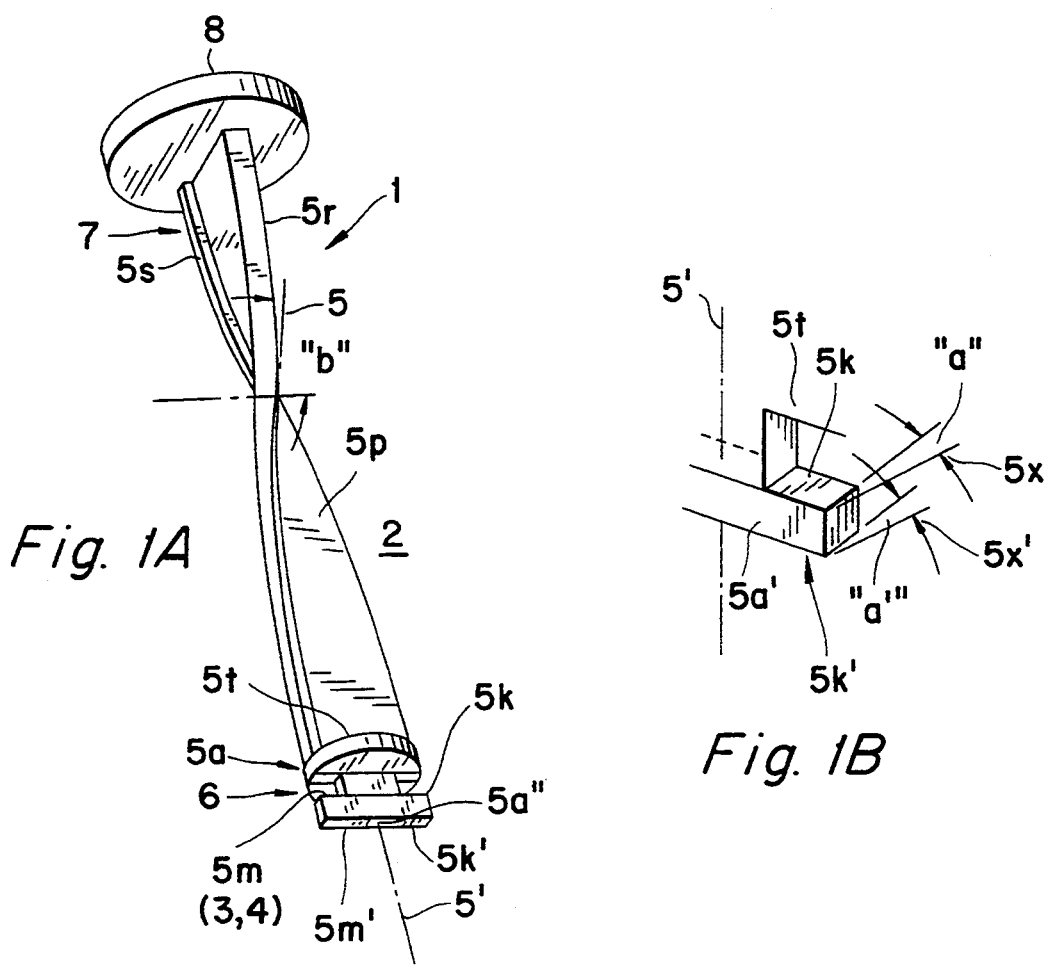
Fig. 1A
Fig. 1B
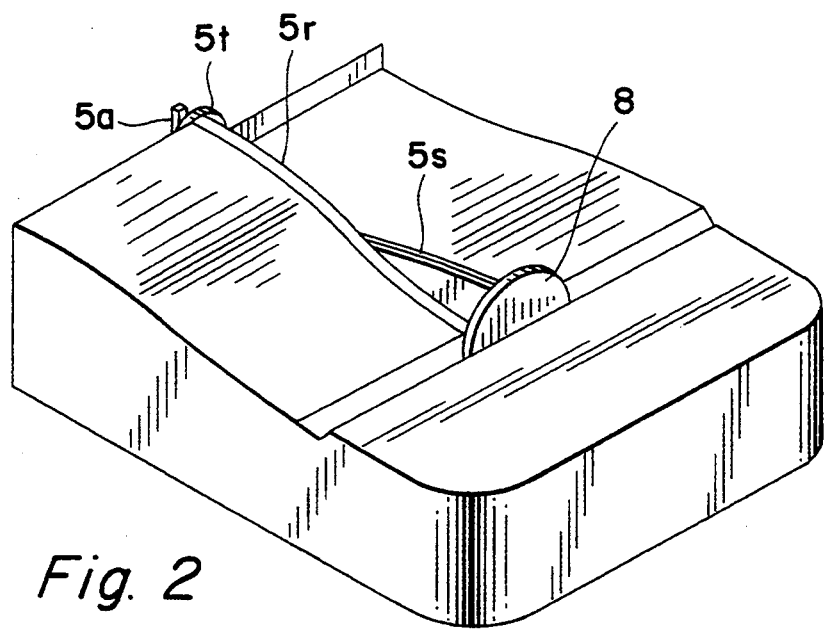
Fig. 2

SYRINGE, HAVING A ROD AND A PISTON AND A DISCONNECT MECHANISM

TECHNICAL FIELD

The present invention relates to a syringe, and then particularly to a disposable syringe intended for one-time-use only.

The invention particularly pertains to the rod and the piston that forms part of the syringe and to the use of a special coupling or a special means for controlling coaction between these syringe components.

The present invention relates to, or encompasses, a rod which forms part of a syringe intended for the injection of a liquid. A syringe of this kind comprises a container a needle, a piston and the aforesaid rod, and also a means for connecting and disconnecting the piston to and from the rod.

Thus, the invention relates particularly to the configuration of the rod and to the configuration of a means which connects and disconnects the rod to and from the piston, said rod being intended to form part of a syringe with which said means shall be brought to a connecting or coupling state when the piston is initially withdrawn by the rod from a position close to the needle to a position in which it is distanced from the needle, and is brought to a disconnected or uncoupled state when the piston is urged forwards by the rod through an adapted, small distance in a direction towards the needle.

The invention constitutes a further development of a previously known rod which forms part of a syringe intended for the injection of a liquid, wherein the rod is intended to coact with the container in a manner to twist the rod when it is moved in relation to the container, and wherein, in order to form said means, that part of the rod which faces towards the needle is provided with support surfaces which are intended to coact with opposing support surfaces on the piston.

The present invention also relates to, or encompasses, a piston which forms part of a syringe intended for the injection of a liquid. This syringe is comprised of a container, a needle, the piston and a rod, and also a means which functions to connect and disconnect the piston to and from the rod.

Thus, the invention relates particularly to the configuration of the piston, and particularly to the configuration of the aforesaid piston connecting and piston disconnecting means intended to form part of a syringe in which said means is intended to be brought to a connecting or coupling state when the piston is withdrawn by the rod from a position in which it is located close to the needle to a position in which it is distanced from said needle, and to be brought to a disconnected state when the piston is urged by the rod through an adapted, small distance in a direction towards the needle.

The invention constitutes a further development of a previously known piston which forms part of a syringe intended for the injection of a liquid, wherein the piston is intended to coact with the container in a manner such as to be moved rectilinearly when the piston is moved relative to the container by a twistable rod, and wherein, for the purpose of forming said connecting and disconnecting means, that part of the piston remote from the needle is provided with support surfaces which are intended to coact with opposing support surfaces on the rod.

BACKGROUND OF THE INVENTION

A disposable syringe for liquid injection on which the present invention can be said to be based is described in detail in the U.S. Pat. No. 5,032,114, which illustrates a syringe of the kind described in the introduction and with which the means which functions to connect and disconnect the piston to and from the rod has a screw thread configuration. The embodiments of the rod disconnecting and connecting means described in this international patent application in FIGS. 6 and 9 can be said to constitute the closest relevant prior art.

Other disposable injection syringes are also known to the art, for instance the syringe described and illustrated in Swedish Patent Publication SE-B-79 02138-2, publication No. 438 598.

The injection syringe described and illustrated in the European Patent Publication EPA2-0 229 017 also forms part of the prior art.

Also forming part of the known art is the rod configuration described in publication U.S. Pat. No. 5,004,460 and illustrated in FIG. 7 of said publication.

In addition to the aforecited publications, reference is also made to the piston and rod coupling means illustrated and described in patent publications U.S. Pat. No. 4,906,231, FR-A-2 381 527 and NO-A-163 263.

DISCLOSURE OF THE PRESENT INVENTION

TECHNICAL PROBLEMS

When studying the earlier known art relating to disposable syringes intended for the injection of a liquid, it will be evident that a technical problem resides in the providing conditions and a rod configuration which will enable the rod to be produced by plastic molding techniques or like techniques to a degree of accuracy and a mutual fit with the piston that will fulfill the requirement of good functioning.

It will also be seen, particularly when taking into consideration the prior art taught by the aforesaid U.S. Pat. No. 5,032,114, that a technical problem also resides in the provision of a rod provided with piston connecting and disconnecting means which can be readily manufactured in conjunction with the rod when manufacturing said rod by injection molding in a plastic molding machine having a two-part die or matrix.

It will also be seen that a technical problem resides in realizing along which lines along the rod and the connecting and disconnecting means said die parts shall coact, in order to enable and facilitate plastic molding of the rod with said connecting and disconnecting means formed integrally therewith, in a rational fashion.

When considering the aforesaid, it will also be seen that a technical problem resides in configuring or designing a rod terminating section positioned adjacent the piston or the needle and to provide said disconnecting and connecting means with support surfaces and/or slide surfaces and to realize that these surfaces should be inclined, within given limits, so as to achieve a satisfactory connecting and disconnecting function between rod and piston.

It will also be seen that a further technical problem resides in realizing how and within which angular values these surfaces should be inclined in order to ensure reliable disconnection of the rod from the piston in response to a small, adapted twisting movement of the rod and solely rectilinear movement of the piston.

Another technical problem which will be apparent from the aforegoing within the application recited is one of realizing the significance of coordinating a selected angle of inclination for the surfaces on the rod with selected inclination of opposing surfaces on the piston.

Another technical problem is one of not only realizing the angular values that should be chosen, but also of providing connecting and disconnecting means which are adapted and configured with view to the manufacturing technique used, said means having a short screw thread configuration with a pitch which conforms to but which is much smaller than the pitch of the rod.

In order to achieve good functioning, another technical problem is one of choosing the pitch of the screw thread configuration between support and/or slide surfaces included in said means with a starting point from selected rotation or twisting of the rod.

Another technical problem is one of realizing that when applying a simplified manufacturing technique for production of the rod in a two-part die, it is necessary to assign the rod a very limited rotational movement, or twisting movement, and therewith realize the maximum angular value permitted for this rotational movement.

Another technical problem is one of providing a rod of such cross-section and of such configuration as to enable the rod to be comprised of thin plastic material but nevertheless exhibit sufficient flexural rigidity to ensure a positive function.

It will also be seen that a further technical problem resides in realizing the significance of and the possibility associated with permitting the rod, adjacent said connecting and disconnecting means, in the form of a T-shaped rod terminating section, to present a disc-like member formed integrally with the rod and serving as a guide against the inner wall of the container.

When considering the possibility of injection molding the rod, preferably from a thermoplastic material in a two-part die, it will be seen that when bearing in mind the desirability of affording sufficient rotation a further technical problem is one of realizing that this rotation or twisting of the rod should be slightly smaller than 90°, and also that the length of the support and/or slide surfaces forming said connecting and disconnecting means must be adapted so as to afford an aspiring path along which the rod and the piston can be moved backwards and forwards through an adapted small distance, without loosing mutual coaction, one with the other.

When considering the known prior art with regard to a disposable syringe intended for the injection of a liquid, it will be seen that a technical problem is one of providing conditions and a piston configuration, and also the piston connecting and disconnecting means which will enable the same to be produced by plastic molding techniques or the like, to a degree of accuracy and a mutual fit with the rod which will fulfill the requirement of good functioning.

It will then also be seen, particularly when considering the prior art taught by the aforesaid U.S. Pat. No. 5,032,114, that a further technical problem resides in the provision of a piston provided with piston connecting and disconnecting means which can be manufactured readily in conjunction with the piston, when the piston is manufactured by injection molding in a plastic molding machine in a two-part die.

When considering the aforesaid, it will also be seen that a technical problem resides in configuring or designing the piston and its section orientated from the piston or the needle so as to enable said connecting and disconnecting means to be produced in the form of support and/or slide surfaces on the piston, and to realize that at least some of these surfaces should be inclined within given limits in order to achieve satisfactory connecting and disconnecting function between rod and piston.

In this regard, another technical problem is one of realizing how these surfaces should be inclined and within which angular values in order to ensure that a positive and reliable disconnection will be obtained between rod and piston when the rod is twisted or rotated through a small angle and the piston moves only rectilinearly.

It will also be seen that a technical problem within the recited field of application is one of realizing the significance of coordinating selected angles of inclination on the piston surfaces with selected angles of inclination on the coacting rod surfaces.

In addition to realizing the values within which these angles of inclination should be chosen, another technical problem is one of providing for said connecting and disconnecting means a suitable configuration which is adapted to the manufacturing technique used, this configuration possibly including a short screw thread form with a pitch that conforms to but which is much smaller than the pitch of the rod.

It will also be seen that another technical problem is one of providing a piston cross-section and a piston configuration which will enable the piston to be manufactured from plastic material while exhibiting sufficient rigidity with regard to said connecting and disconnecting means, in the form of peripherally disposed and outwardly extending wall parts.

SOLUTION

The present invention relates to a disposable syringe and is based on the known syringe described in the introduction and having the features set forth in claim 1.

The present invention therewith relates to a novel form of a rod intended to form part of a syringe intended for the injection of a liquid, and particularly to a disposable syringe of the kind which comprises a container, a needle, a piston and said rod and which also includes means for connecting and disconnecting the piston to and from the rod, wherein said means is brought to a connecting or coupling state when the piston is withdrawn by the rod from a position in which it is located close to the needle to a position in which it is distanced from said needle, and is brought to a disconnecting or uncoupling state when the piston is urged by the rod through a small, adapted distance in a direction towards the needle, wherein the rod is intended to coact with the container in a manner such that when the rod is displaced relative to the container, said rod is twisted, or rotated, relative to the container and the piston, and wherein the bottom part of the rod facing towards the needle is provided with support and/or slide surfaces which are intended to coact corresponding surfaces on the rod.

In accordance with the present invention, the rod of this earlier known kind and forming part of a liquid injection syringe is permitted to rotate, or twist, continuously along the whole of its length through an angle of not more than 90° or thereabouts, and in that the rod has an angled cross-section.

According to proposed embodiments, the rod has an angled cross-section with a thin, planar centre part and with at least one flexural-strength-enhancing edge. Preferably, the cross-sectional shape of said rod will exhibit two such edges which extend away from one another.

It is also proposed that the support and/or slide surfaces on the rod forming part of said connecting and disconnecting means are inclined slightly in a direction conforming to the direction of movement of the rod downwards towards the needle and are formed peripherally to a T-shaped rod terminating section.

Further embodiments of the invention also include the provision of mutually opposed, peripheral piston support and/or slide surfaces at mutually the same angle of inclination or slope.

It is also suggested that the T-shaped rod-terminating section is located adjacent an overlying disc-like member having a diameter which is only slightly smaller than the inner diameter of the container.

Finally, it is also proposed that the support and/or slide surfaces are comprised of two upper and two lower peripherally orientated surfaces.

The present invention also relates to a novel type of piston forming part of a syringe intended for the injection of liquid, and then particularly to a disposable syringe, and is based on a syringe of this kind which comprises a container, a needle, said piston and a rod, and further comprises means for connecting and disconnecting the piston to and from the rod, wherein said means are constructed to be brought to a connecting state when the piston is withdrawn by the rod, in response to a twisting movement, from a position close to the needle to a position distanced from said needle, and is brought to a disconnecting state when the piston is moved by a twistable rod rectilinearly through a small, adapted distance in a direction towards the needle, wherein the rod is intended to coact with the container in a manner such that when moved axially in relation to the container, the rod will twist or rotate in relation to the container and piston, and wherein the bottom part of the rod that faces towards the needle is provided with support and/or slide surfaces perpendicular, or at least essentially perpendicular, to a centre line on the rod, said surfaces being intended to coact with corresponding surfaces on the piston.

According to the present invention, this earlier known liquid injection syringe is improved by inclining the support and/or slide surfaces on the piston in a direction relating to the movement direction of the rod, said surfaces being formed peripherally in relation to the piston.

According to proposed embodiments which lie within the scope of the inventive concept, the opposed peripheral surfaces on the piston are formed in a peripheral wall section.

The slope or inclination shall preferably have the form of part of a screw thread of restricted length along the periphery and having an angular value of less than 25°.

For the purpose of providing an aspiring function, it is also proposed that the rod is able to move and rotate axially to a limited extent in relation to the container and the piston, backwards and forwards, without the connecting and disconnecting means on the rod releasing their coacting contact with the piston connecting and disconnecting means.

ADVANTAGES

The advantages primarily afforded by the inventive disposable syringe is that the rod is configured in a manner which will enable it to be manufactured rationally from plastic components molded in a die or matrix, and that the rod/piston connecting and disconnecting means have a configuration, or shape, which is adapted to said rational method of manufacture.

According to the invention, the main advantages afforded by a disposable syringe and a piston included in a syringe intended for the injection of a liquid are that the piston components, including the rod and piston connecting and disconnecting means have a shape or configuration suitable for injection molding or light techniques.

The primarily characteristic features of an inventive syringe are set forth in the characterizing clause of claim 1.

The primary characteristic features of a rod forming part of a liquid injection syringe in accordance with the present invention are set forth in the characterizing clause of claim 2.

The main characterizing features of a piston forming part of an inventive liquid injection syringe are set forth in the characterizing clause of claim 10.

BRIEF DESCRIPTION OF THE DRAWINGS

An exemplifying embodiment at present preferred and having features characteristic of the present invention will now be described in more detail with reference to the accompanying drawings, in which FIG. 1A is a perspective, enlarged view of a section of a rod adapted for a container (not shown), and FIG. 1 shows support and/or slide surfaces on said rod, arch, which are intended for coaction with corresponding support and/or slide surfaces on a piston;

FIG. 2 is a perspective view of one-half of a two-part mold insert which functions as a die for use when injection molding or die casting a rod and associated means;

DESCRIPTION OF EMBODIMENTS AT PRESENT PREFERRED

Figure 3A:
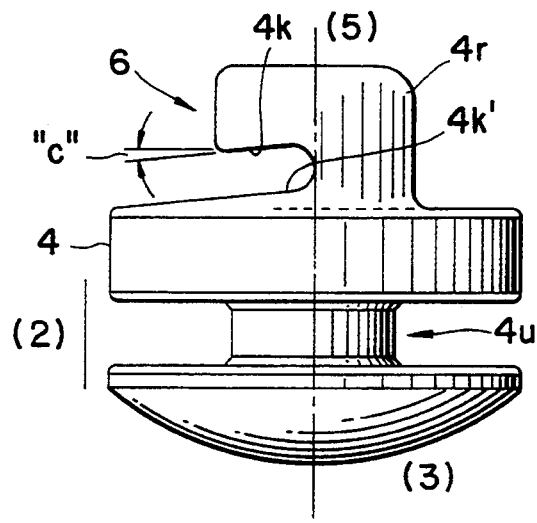
FIG. 3A and 3B illustrate in side view and in enlarged scale a piston having a groove in which the terminating end section of the rod is intended to fit, said groove functioning as a piston and rod connecting and disconnecting means.

Since the present invention is a direct development of the syringe and the rod described and illustrated in the aforesaid U.S. Pat. No. 5,032,114, reference is made to this publication, which is intended to constitute part of the description of the present invention, in order to illustrate the function of a disposable syringe provided with rod and piston connecting and disconnecting means.

Thus, FIG. 1 illustrates in perspective a rod-like element 5, which is adapted for insertion into a container 2 (not shown in FIG. 1) and the bottom part of which, i.e. the part facing towards a needle 3 (not shown in FIG. 1) is adapted for coaction with connecting and disconnecting means on a piston 4.

The present invention thus relates to a novel rod of novel construction and novel configuration for inclusion in a disposable syringe 1 intended for the injection of liquid. This syringe comprises a container 2, a needle 3, a piston 4 and the rod 5, and also means 6 which function to connect and disconnect the piston to and from the rod.

The connecting and disconnecting means 6 are brought to a piston connecting position, or state, when the piston 4 is withdrawn by the rod 5 from a position close to the needle 3 to a position where it is distanced from the needle. The means 6 are brought to a disconnecting position, or state, when the piston 4 is urged by the rod 5 through a short, adapted distance in a direction towards the needle 3, wherein the rod 5 is intended to coact with the container 2 in a manner such that when moving relative to the container, the rod will be twisted, or rotated, in relation to the container 2 and the piston 4, which executes a rectilinear movement.

The part 5a of the rod 5 facing towards the needle 3 is provided with upper support surfaces 5k, 5m, which are perpendicular, or at least generally perpendicular, to a rod centre line 5′ and which are disposed to face upwards or away from the needle 3 and are intended to coact with oppositely located support surfaces on the piston 4.

The rod part 5a facing the needle 3 is also provided with bottom or lower support surfaces 5k′, 5m′, which are perpendicular, or at least generally perpendicular, to a rod centre line 5′ and which face downwards or towards the needle 3, these support surfaces 5k′, 5m′ being intended for coaction with oppositely located support surfaces on the piston 4.

Depending on the construction chosen, the tolerances obtained and the chosen direction of movement, the aforesaid "support surfaces" will not only function as piston support surfaces but also as slide surfaces acting between the respective connecting and disconnecting means on the rod and the piston.

For example, it can be assumed that when moving the piston away from a position close to the needle 3 to an upper position, the surfaces 5k, 5m will function solely as support surfaces, but when the rod is moved up and down through a shorter distance in an aspiring function, the surfaces will function both as support surfaces and as slide surfaces.

In particular, when the central, lowermost end surface of the rod 5 is provided with a pressure surface 5a″, in the form of a spherical projection or a circular plate of small extension, said surface 5a″ being intended to press against a centrally located support surface on the upper part of the piston, when the rod 5 urges the piston 4 towards the needle 3 and during the terminating movement, the aforesaid surfaces 5k′ and 5m′ will primarily function as support surfaces which position the piston correctly and which are intended to support against the periphery of the piston and therewith prevent the piston from tilting.

It has been found highly beneficial to slightly incline at least the upper surfaces 5k, 5m on the rod 5 in a direction conforming with the direction of rotation of the rod, i.e. the direction of rotation in which the rod 5 is moved towards the needle 3, through an angle "a" and to give these surfaces e peripheral, inverse T-shape on the terminating rod section 5a′.

The value of the angle "a" shall be smaller than 25°, preferably between 5-15° in relation to a selected horizontal plane 5x. The bottom support surfaces 5k′ and 5m′ on the rod 5 may also be inclined slightly downwards at an angle of "a′" and these surfaces are also formed peripherally on the rod terminating section 5a′.

The value of the angle "a′" will preferably be the same as that of the angle "a" in relation to a chosen horizontal plane 5x′.

The angular value of the rod, referenced "b" is between 70° and 80°.

The oppositely located surfaces on the piston have the same angle of inclination as those on the rod.

As shown in FIG. 1, the rod 5 is intended to be twisted through an angle, which from the aspect of practical manufacture, must be slightly less than 90°, and because the largest possible angle of rotation is desired, it is proposed that the angle through which the rod can rotate, or twist, is at least greater than 80°.

Seen practically and when using a two-part die or mould, this angular value is preferably 88°-89°.

The rod has an angled cross-sectional shape and exhibits a broad central and thin part 5p, having formed integral therewith stiffening edges 5r, 5s, which extend away from one another and which are equally as thin as said broad part 5p.

The T-shaped rod terminating section 5a′ is located adjacent a disc-shaped member 5t whose diameter is only slightly smaller than the inner diameter of the container 2, said disc therewith forming means for guiding the bottom part of the rod in relation to the container.

By selecting the angles "a" and "b" in the manner aforesaid, an aspiration distance is provided by the angular difference of the transverse extension of the support surfaces 5k, 5m and on the length of the oppositely located support surfaces on the piston, which enables the rod to be moved reciprocatingly through an adapted, small distance in response to a small twisting movement, without the respective connecting and disconnecting means 6 relinquishing their mutual coaction when the piston moves in a straight line.

The whole of the rod 5 is manufactured in one piece, among other things, with an integrated upper pressure plate 8.

FIG. 2 illustrates in perspective one-half of a two-part mold insert which functions as a die or mould, and further illustrates where a selected interface line or border between the die parts shall be placed in order to produce, in one working operation, the rod with said integrated, upper pressure plate, an adapted angle of rotation, a lower disc and said associated connecting and disconnecting means.

Figure 3B:
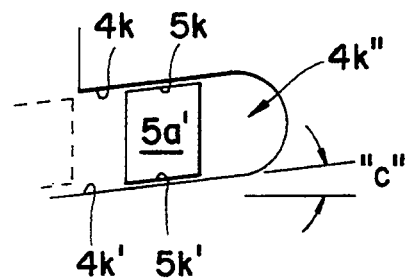

FIG. 3 is a side view of a circular piston 4 adapted for insertion into a container 2 (not shown in FIG. 1) and the upper part of which, i.e. the part facing away from the needle 3 (not shown) is adapted for coaction with connecting and disconnecting means on a rod.

Thus, the present invention relates to a piston of novel configuration and construction for use in a disposable syringe intended for the injection of a liquid. The syringe is comprised of a container 2, a needle 3, said piston 4, a rod 5 and means for connecting and disconnecting the piston to the rod.

The part 5a of the rod 5 facing towards the needle 3 is also provided with bottom support surfaces 5k', 5m' which extend perpendicularly or at least essentially perpendicularly to a centre line on the rod and which face downwardly or towards the needle 3, said support surfaces 5k', 5m', being intended to coact with oppositely located support surfaces 4k' and 4m' respectively on the piston 4.

As shown in FIG. 3, the groove is intended to extend slightly upwards and has parallel surfaces 4k and 4k'.

The value of the angle "c" shall be less than 25°, preferably between 5°–15°.

The oppositely located support surfaces 4k, 4m on the piston 4 have the same angle of inclination as the support surfaces 5k, 5m on the rod.

The surface extension of the rod and the piston support surfaces has the form of a screw thread or is flat and of very limited length.

The choice of the angle of inclination is significant in ensuring a necessary sliding action between rod and piston, so that the rod can be twisted without the piston taking part in the twisting movement.

The piston shall move in a straight line in the container.

In order to afford limited movement of the rod 5 up-and-down in relation to the container 2 while maintaining coaction with the piston 4, there is provided the possibility of performing an aspiration function. The connecting and disconnecting means 5a' on the rod shall be able to slide and rotate relative to the connecting and disconnecting means on the piston in the form of a groove, said piston following this limited movement rectilinearly.

The maximum permitted length of said movement distance while retaining said coaction will depend on the angle through which the rod is twisted, the length of the groove in the piston and its angle and the width of the T-shaped rod terminating section 5a'.

In practice, this movement distance should be from 2–5 mm.

It will be obvious that this limited axial movement of the rod 5 and the piston 4 connected thereto, up-and-down in the container 2, will mean that the means for connecting and disconnecting the piston to and from the rod will constantly have a connecting position. The aforesaid means 6 are not brought to a disconnecting position until the rod 5 and the piston 4 have moved beyond the distance of said limited movement towards the needle, in that the right edge of the support surface 5k on the rod, FIG. 3, moves out of engagement with the left edge of the support and/or slide surface 4k on the piston 4.

This is shown more clearly in FIG. 3 in a broken-line position, where it is also illustrated that the support surface 4k' has an angular value "c" which corresponds precisely to the angular value of the rod. Also shown in FIG. 3, in full lines, is a position in which the rod has been moved axially towards the needle 3 through a small distance, therewith rotating the support surface 5k out of coaction with the support surface 4k.

The support surface 5k' has been rotated into sliding coaction with the surface 4k' and the piston 4 is urged downwardly while the rod rotates the section 5a' out of engagement with the groove.

In the full line position shown in FIG. 3, the piston 4 can again be moved by the rod 5 away from the needle 3, through the contact surface afforded by the support surfaces 5k and 4k. A further, small movement towards the needle 3, however, will cause the support surface 5k to move out of contact with the surface 4k causing further movement of the rod 5 away from the needle 3 and thereby causing the rod terminating section 5a' to leave its position of coaction with the piston 4 and the piston 4 will thus be pressed solely in one single direction, namely towards the needle (3).

Upon completion of an injection with the piston 4 located nearest the needle, the syringe can thus again become the subject for a new injection.

Figure 4:
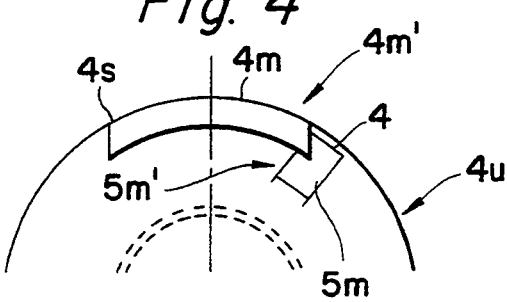
FIG. 4 is a horizontal view of part of the piston, showing associated support and/or slide surface and a complementary support and/or slide surface on the rod.
Figure 5A:
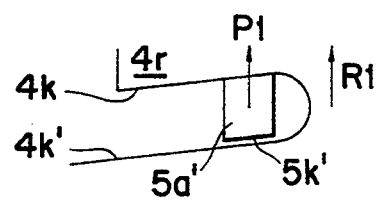
FIGS. 5A through 5E illustrate the piston and rod connecting and disconnecting means in different positions during part of a forwards and backwards movement.
Figure 5B:
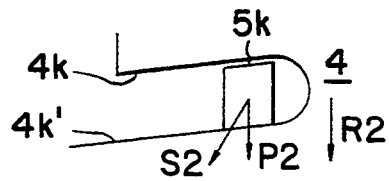
Figure 5C:
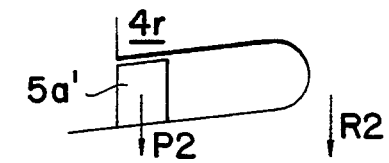
Figure 5D:
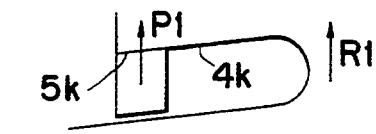
Figure 5E:
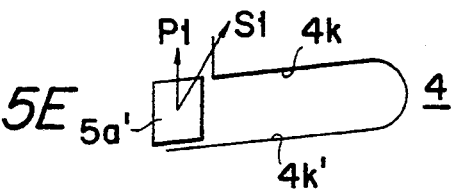

As illustrated in FIGS. 3 and 4, the piston 4 is provided peripherally with diametrically positioned projections 4r and 4s, or wall parts, and a web 4u which is intended to support a sealing ring (not shown) for sealing coaction with the container 2.

The projection 4r is provided with a recess or a groove forming support surfaces 4k and 4k' and the projection 4s is provided with a corresponding, but turned, recess or groove forming support surfaces 4m and 4m'.

FIG. 5 illustrates a sequence A–E of positions taken by the piston and the rod connecting and disconnecting means during part of a cycle, with the tolerances being exaggerated for the purpose of illustration.

The sequence A is intended to show that when acted upon by a force in the direction of the arrow P1, the rod terminating section 5a' causes the piston to accompany movement in the direction of the arrow R1, and that the angular value of the surface 4k is selected so that the rod terminating part 5a' will be located at the bottom of the groove.

The sequence B is intended to show that when the rod terminating section 5a' is urged in the direction of the arrow P2, it will lie against the surface 4k' and when displaced in the direction of the arrow S2, the piston 4 will move downwards, without rotating.

When the rod terminating section 5a' is in the position shown in sequence C, the rod 5 can be moved in the opposite direction, according to the arrow P1, sequence D being intended to illustrate this movement.

This movement presses the surface 5k against the surface 4k and in response to movement in the direction of the arrow s1, the piston 4 will move upwards, without rotating. In an aspiration cycle, piston and rod are turned upside down.

FIG. 4 is a partial cross-sectional view taken through projection 4s and directed toward the needle 3.

When the rod terminal section 5a' is moved to the position shown in sequence E, said section will have moved out of coaction with the groove, with the surfaces 4k and 4k', and the piston 4 can only be moved towards the needle by the rod 5.

Figure 6:
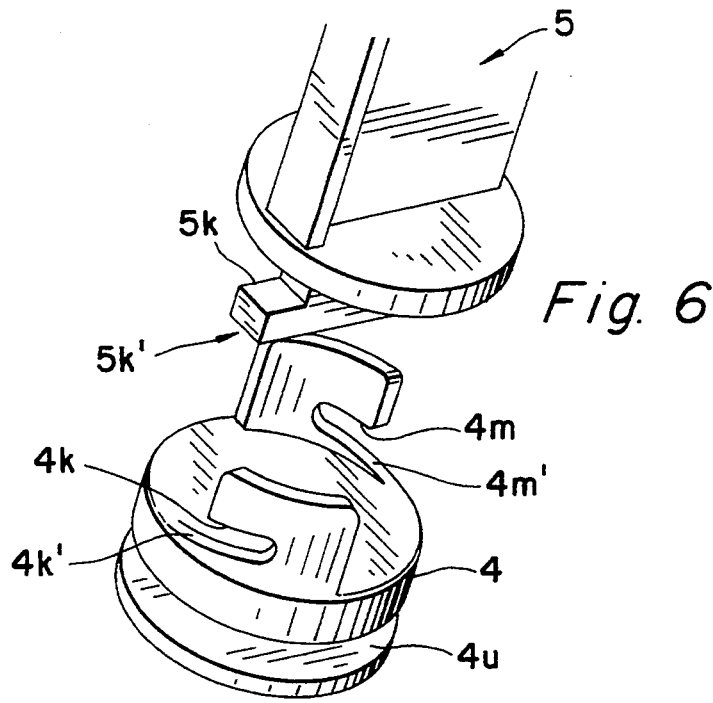
FIG. 6 illustrates in perspective the connecting and disconnecting means of the piston and the rod respectively when said means are in engagement with one another.

FIG. 6 illustrates in perspective the respective piston and rod connecting and disconnecting means in a position where they are not in engagement with one another and the rod 5 is only able to urge the piston 4 towards the needle.

Figure 7A:
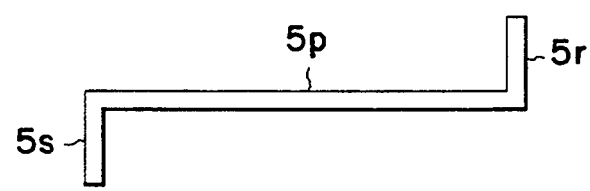
FIGS. 7A through 7C illustrate different embodiments of the rod cross-section.

The illustrated rod has a Z-shaped cross-section, presenting a broad central part 5p and two mutually opposed edges 5s and 5r, according to FIG. 7A of similar cross-section.

Figure 7B:
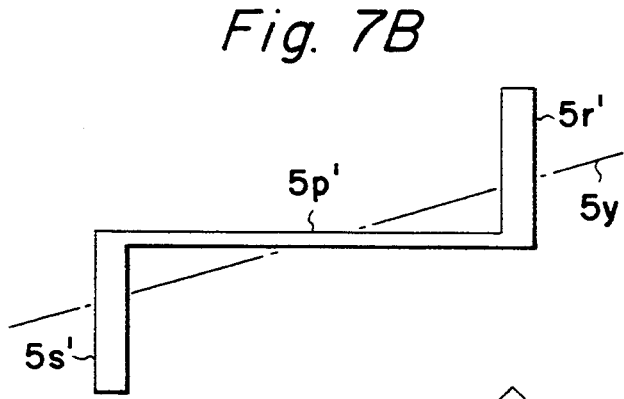

Within the framework of the same material consumption, and possibly less material consumption, it is possible to make the central part 5p' thinner and the edges 5s' and 5r' longer and even thicker than the central part shown in FIG. 7B.

Figure 7C:
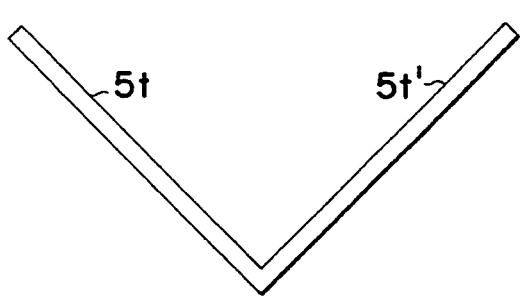

FIG. 7C illustrates a V-shaped or a L-shaped cross-section, with the parts 5t and 5t' forming a right angle and having a similar cross-section.

It lies within the scope of the invention to manufacture rod 5 in a two-part die while obtaining sufficient resistance to bending about a bending line with least bending resistance, such as the bending line 5y in FIG. 7B, for a given application. It will be understood that a selected cross-section will also afford other cross-sectional shapes and other mass distributions than those illustrated in FIGS. 7A, 7B and 7C.

The invention is not restricted to the aforedescribed and illustrated exemplifying embodiment thereof, since modifications and changes can be made within the scope of the inventive concept as defined in the following claims.

We claim:

1. A syringe comprising a container a rod which can be moved reciprocatingly relative to said container, one end of which container forming means to coact with a needle, and a piston which coacts with the rod, said rod comprising:
    means for connecting and disconnecting the piston to and from the rod;
    said connecting and disconnecting means including a T-shaped bar having piston support surfaces facing toward a piston end of the rod;
    said piston support surfaces extend substantially perpendicular to a center line on the rod and are inclined in a direction of rotational movement relative to said center line of the rod;
    said piston support surfaces arranged so as to coact with similarly angled support surfaces on the piston;
    wherein said connecting and disconnecting means are brought to a connecting position relative to said piston when the piston is drawn by the rod away from the needle, and are brought to a disconnecting position relative to said piston when the piston is urged by the rod in a direction towards the needle; and
    said syringe further including means for the rod to coact with the container in a manner such that when the rod is moved axially in relation to the container the rod is rotated through an angle about said center line in relation to said container.

2. The syringe of claim 1, wherein said piston support surfaces are inclined in a direction of movement of the rod at an angle of less than 25°.

3. The syringe of claim 1, wherein said piston support surfaces are inclined in a direction of movement of the rod at an angle of 5°–15°.

4. The syringe of claim 1, wherein said piston support surfaces are comprised of two surfaces, said T-shaped bar further including two surfaces facing away from said piston end of the rod.

5. The syringe of claim 1, wherein said rod has an angular cross section, a broad central thin part, and stiffening edges which extend from said broad central thin part.

6. A piston for forming part of a syringe, said syringe including a container and a rod which rod can be moved reciprocatingly relative to said container, one end of which container forms a means to coact with a needle, said piston for coacting with the rod, said piston comprising:
    means for connecting and disconnecting the piston to and from the rod;
    said connecting and disconnecting means including opposite peripheral projections having rod support surfaces facing toward a rod end of the piston;
    said rod support surfaces extending substantially perpendicular to a center line on the piston and are inclined in a direction of rotational movement relative to said center line of the piston;
    said rod support surfaces arranged so as to coact with similarly angled support surfaces on the rod;
    wherein said connecting and disconnecting means are brought to a connecting position relative to said rod when the piston is drawn by the rod away from the needle, and are brought to a disconnecting position relative to said rod when the piston is urged by the rod in a direction towards the needle.

7. The rod of claim 6, wherein said piston support surfaces are inclined in a direction of movement of the rod at an angle of less than 25°.

8. The rod of claim 6, wherein said piston support surfaces are inclined in a direction of movement of the rod at an angle of 5°–15°.

9. The rod of claim 6, wherein said piston support surfaces are comprised of two surfaces, said opposite peripheral projections further including two surfaces facing away from a rod end of the piston.

10. The piston of claim 6, wherein said rod has an angular cross section, a broad central thin part, and stiffening edges which extend from said broad central thin part.

* * * * *